United States Patent [19]

Dubief et al.

[11] Patent Number: 5,786,310
[45] Date of Patent: Jul. 28, 1998

[54] SYNTHETIC OIL-BASED WASHING COMPOSITIONS AND METHOD OF USE

[75] Inventors: Claude Dubief, Le Chesnay; Daniele Cauwet, Paris, both of France

[73] Assignee: L'Oreal, Paris, France

[21] Appl. No.: 464,543

[22] Filed: Jun. 5, 1995

Related U.S. Application Data

[62] Division of Ser. No. 176,693, Jan. 3, 1994, abandoned, which is a continuation of Ser. No. 836,727, Feb. 19, 1992, abandoned.

[30] Foreign Application Priority Data

Feb. 19, 1991 [FR] France .................. 91 01954

[51] Int. Cl.$^6$ .................. C11D 3/18; C11D 1/02; C11D 1/66
[52] U.S. Cl. .................. 510/122; 510/122; 510/123; 510/125; 510/127; 510/470; 510/466; 510/432; 510/129
[58] Field of Search .................. 252/167, 174.17, 252/174.13; 510/122, 123, 125, 127, 470, 466, 432, 129

[56] References Cited

U.S. PATENT DOCUMENTS

| | | | |
|---|---|---|---|
| 2,528,378 | 10/1950 | Mannheimer et al. | 252/546 |
| 2,781,354 | 2/1957 | Mannheimer et al. | 252/546 |
| 4,421,656 | 12/1983 | Donatelli et al. | 252/8.6 |
| 4,454,316 | 6/1984 | Veeder et al. | 536/123 |
| 4,676,920 | 6/1987 | Culshaw | 252/163 |
| 4,741,855 | 5/1988 | Grote et al. | 252/142 |
| 4,913,828 | 4/1990 | Caswell et al. | 252/88 |
| 4,954,335 | 9/1990 | Janchipraponvej | 424/70 |
| 4,997,641 | 3/1991 | Hartnett et al. | 252/547 |
| 5,011,681 | 4/1991 | Ciotti et al. | 424/81 |
| 5,051,250 | 9/1991 | Patel et al. | 424/70 |
| 5,078,990 | 1/1992 | Martin et al. | 424/70 |
| 5,151,210 | 9/1992 | Steuri et al. | 252/174.017 |
| 5,286,476 | 2/1994 | Nanba et al. | 424/47 |

FOREIGN PATENT DOCUMENTS

| | | |
|---|---|---|
| 1000757 | 3/1989 | Belgium . |
| 023397 | 2/1981 | European Pat. Off. . |
| 064354 | 11/1982 | European Pat. Off. . |
| 079038 | 5/1983 | European Pat. Off. . |
| 127698 | 12/1984 | European Pat. Off. . |
| 217250 | 4/1987 | European Pat. Off. . |
| 226250 | 6/1987 | European Pat. Off. . |
| 351303 | 1/1990 | European Pat. Off. . |
| 2596061 | 9/1987 | France . |
| 2633940 | 1/1990 | France . |
| 2058106 | 4/1981 | United Kingdom . |
| 2058107 | 4/1981 | United Kingdom . |
| 2164658 | 3/1986 | United Kingdom . |

OTHER PUBLICATIONS

CA 107:83684 "New Possibilities of Viscosity Adjustment of Cosmetic Products," Hamke Meijer, 1987 (no month available).

*Primary Examiner*—Paul Lieberman
*Assistant Examiner*—Charles Boyer
*Attorney, Agent, or Firm*—Jacobson, Price, Holman & Stern, PLLC

[57] ABSTRACT

The subject of the present invention is compositions for washing keratinous materials, in particular the hair and/or the skin, containing in an aqueous medium:

A) at least one synthetic oil chosen from:

the isoparaffins of the formula:

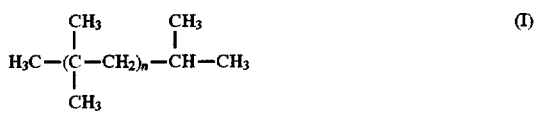

where n is between 2 and 16 inclusive;

B) an agent for suspending the oil defined under A), chosen from:

(i) the compounds of formula:

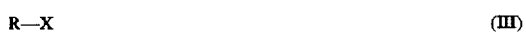

in which:

R is a long carbon chain aliphatic radical, optionally interrupted by one or more oxygen atoms, and X is a carboxylic, sulphuric or phosphoric acid residue or a radical derived from a carboxylic acid or an amide;

(ii) amine oxides;

(iii) biopolysaccharides;

C) a surface-active agent possessing detergent properties.

2 Claims, No Drawings

SYNTHETIC OIL-BASED WASHING COMPOSITIONS AND METHOD OF USE

This is a division of application Ser. No. 08/176,693, filed Jan. 3, 1994, abandoned, which is a continuation of application Ser. No. 07/836,727, filed Feb. 19, 1992, abandoned.

The invention relates to compositions for washing and conditioning keratinous materials, in particular the hair and/or the skin, and containing, in an aqueous medium, at least one synthetic oil in the presence of agents for suspending this oil and detergent surface-active agents, and to the methods of washing using these compositions.

Compositions for washing keratinous materials, in particular shampoos, are well known in the state of the art.

It has already been proposed to use oils in such compositions, in particular in the treatment of dry hair for the purpose of conferring softness and sheen thereto.

Because of the insoluble nature of these synthetic oils in the-aqueous media generally used in washing compositions such as shampoos, it is sought to maintain these oils in a dispersed form while preserving the detergent and foaming properties of the composition without causing a drop in the viscosity. These compositions must also confer on the hair the desired qualities of softness, sheen and disentanglement.

The applicant has discovered, surprisingly, that it is possible to prepare washing compositions which are particularly stable with time and possessing good detergent properties while conferring on the hair sheen, softness, ease of combing without a sticky feel, by using in these compositions, in addition to the detergent surface-active agents, specific agents for suspending these synthetic oils.

In addition, it has been observed that these compositions do not possess the disadvantage of making the hair lank when they are used repeatedly.

The compositions conforming to the invention possess, moreover, the advantage of being capable of being prepared without difficulty by means of conventionally used methods and materials.

The subject of the invention is therefore a washing composition containing at least one synthetic oil, at least one agent for suspending this oil and at least one detergent surface-active agent.

Another subject of the invention consists in the use of the suspending agents defined below as agents for suspending synthetic oils in an aqueous medium containing detergent surface-active agents.

The subject of the invention is also a method of washing using the compositions defined above.

Other subjects of the invention will emerge from reading the following description and examples.

The washing compositions conforming to the invention contain in an aqueous medium:

(A) at least one synthetic oil chosen from:

(i) the isoparaffins of structure:

$$H_3C-\underset{\underset{CH_3}{|}}{\overset{\overset{CH_3}{|}}{C}}-(CH_2)_n-\overset{\overset{CH_3}{|}}{CH}-CH_3 \quad (I)$$

where n is between 2 and 16 inclusive;

(ii) a mixture of the isoparaffins of formula (I) with isoparaffins of formula (II):

$$H_3C-\underset{\underset{CH_3}{|}}{\overset{\overset{CH_3}{|}}{C}}-(CH_2)_m-\overset{\overset{CH_3}{|}}{CH}-CH_3 \quad (II)$$

where m is not less than 18, and preferably is between 18 and 40;

the capillary viscosity of the oils defined above being less than 500 cP.s;

(B) an agent for suspending the oil, chosen from the compounds of formula:

a) RX  (III)

in which R is a long carbon chain aliphatic radical optionally interrupted by one or more oxygen atoms, and X is a carboxylic, sulphuric or phosphoric acid radical or a radical derived from a carboxylic acid or an amide; these compounds of formula (III) are chosen from those in which:

(i) R is a $C_{11}-C_{21}$ alkyl or alkenyl radical; and X is a COOA group where A is a mono- or polyhydroxyalkyl radical derived from a $C_2-C_3$ polyol or a radical $CH_2CH_2SO_3M$;

a group $CO(OCH_2CH_2)_kOH$ where k has a value of between 2 and 150;

a group $$COOCH_2-\underset{\underset{CH_3}{|}}{CH}-(OCH_2CH_2)_kOH,$$

where k has a value of between 2 and 150, it being possible for the free OH functional groups of the groups defined above to be esterified by an acid RCOOH where R is a $C_{11}-C_{21}$ alkyl or alkenyl;

a group $CONR_1R_2$ where $R_1$ and $R_2$ represent hydrogen or $C_1-C_4$ hydroxyalkyl, at least one representing $C_1-C_4$ hydroxyalkyl;

a group $OSO_3M$ or $\frac{1}{3} PO_4^{3-}M_3$ where M represents an alkali metal, ammonium or a $C_1-C_4$ alkanolamine residue;

(ii) R denotes a radical $R_3O(C_2H_4O)_lCH_2$ and X denotes a group COOM where M has the meaning given above, $R_3$ denoting a $C_{12}-C_{14}$ alkyl radical and l an integer or a decimal between 2.5 and 10, or alternatively $R_3$ denotes oleyl and l ranges from 2 to 9 or alternatively $R_3$ denotes ($C_8-C_9$ alkyl)phenyl and l ranges from 4 to 8, or the derivatives in which $R_3$ denotes a $C_{12}-C_{16}$ alkyl group and X a group $CONR_1R_2$, in which $R_1$ and $R_2$ have the same meaning as that given above and l has a value of 1 to 3 inclusive;

b) amine oxides of formula:

$$R_4-N\overset{R_5}{\underset{\underset{O}{\downarrow}}{\overset{}{\diagdown}}}R_6$$

in which $R_4$ denotes a $C_{16}-C_{22}$ alkyl group, and $R_5$ and $R_6$, which are identical or different, represent a $C_1-C_4$ alkyl or $C_1-C_4$ hydroxyalkyl group;

c) the biopolysaccharides chosen from xanthan gums and scleroglucans;

(C) and a detergent surface-active agent.

Among the synthetic oils of the formula (I) defined above, there may be mentioned those in which n is equal to 2, 3, 4 or 16, and in particular the products sold under the names PERMETHYL 99A, 101A, 102A or 104A by PRESPERSE INC or the product ARLAMOL HD sold by ICI, of the formula (I) in which n is equal to 3.

Among the synthetic oils of formula (II), there may be mentioned the product sold under the commercial name PERMETHYL 106A, of the formula (II) in which m is equal to 38.

Among the preferred suspending agents of formula RX, there may be mentioned:

- the esters of $C_{12}$–$C_{22}$ fatty acids and $C_2$–$C_3$ polyols such as ethylene glycol, propylene glycol or glycerol myristates, palmitates and stearates, and more particularly ethylene glycol monostearate or distearate, or glycerol mono- or distearate or tristearate;
- the alkanolamides of $C_{12}$–$C_{22}$ fatty acids, and more particularly copra or stearic diethanolamide, copra or stearic monoethanolamide, or copra or stearic monoisopropanolamide;
- alkanolamides alkyl ethers such as ($C_{13}$–$C_{15}$ alkyl) oxydiethoxymethylmonoethanolamide such as for example the product sold under the name AMINOL A15 by CHEM'Y;
- polyoxyethylenated $C_{18}$–$C_{22}$ fatty acids such as polyethylene glycol stearates containing between 4 and 150 ethoxy units;
- polyoxyethylenated and esterified esters of $C_{16}$–$C_{22}$ fatty acids and propylene glycol, which may contain between 4 and 100 ethoxy units;
- polyoxyethylenated ether carboxylic acids of the formula $R_3O(C_2H_4O)_lCH_2COOM$ (IV), and among these the products sold under the names AKYPO RLM 38, 25, 45 and 100, for which $R_3$ represents respectively a $C_{12}$–$C_{14}$ alkyl chain and 1 denotes 3.8; 2.5; 4.5 and 10 respectively; the product AKYPO RO 50 for which $R_3$ denotes an oleyl radical and 1 is equal to 5; mixtures of these compounds, and more particularly a mixture of the products AKYPO RO 20 and RO 90 for which $R_3$ denotes oleyl and 1 is equal to 2 and 9 respectively; or alternatively the mixture of the products AKYPO NP 40 and NP 70 in which $R_3$ denotes nonylphenyl and 1 is equal to 4 and 7; or alternatively the products AKYPO OP 40 and OP 80, in which $R_3$ represents octylphenyl and 1 is equal to 4 and 8, the products AKYPO being sold by CHEM'Y.

The amine oxides are for example $C_{16}$–$C_{22}$ alkyl dimethylamine oxides, such as stearyl dimethylamine oxide.

The biopolysaccharides used are products containing glucose, mannose, glucuronic or galacturonic acid, or D-glucopyranose units in their structure.

Xanthan gum, obtained by the action of the bacterium XANTHOMONAS CAMPESTRI and its mutants or variants, having a molecular weight of between 1,000,000 and 50,000,000, may be mentioned among these compounds. Xanthan gums have a viscosity of between 0.60 and 1.65 Pa.s for an aqueous composition containing 1% of xanthan gum, measured in a Brookfield type LVT viscosimeter at 60 revolutions/minute. These gums, which are heterobiopolysaccharides, contain in their structure 3 different monosaccharides which are mannose, glucose and glucuronic acid. The products particularly preferred are those marketed under the name "KELTROL" by KELCO, KELZAN S marketed by KELCO, RHODOPOL 23 SC marketed by RHONE-POULENC, RHODIGEL 23 sold by RHONE-POULENC, DEUTERON XG marketed by SCHOENER GmbH, ACTIGUM CX9 marketed by CECA/SATIA, the products sold by KELCO under the names "KELZAN K3 B130, K8 B12".

Other biopolysaccharides which may be used in accordance with the invention may be chosen from the biopolymer PS 87 produced by the bacterium BACILLUS POLYMYXA which contains in its structure glucose, galactose, mannose, fucose and glucuronic acid; this PS 87 biopolymer is described in the published European Patent Application No. 23397; the biopolymer S88 produced by the strain PSEUDOMONAS ATCC 31554, which contains in its structure rhamnose, glucose, mannose and glucuronic acid; this biopolymer is described in British Patent No. 2,058,106; the biopolymer S130 produced by the strain ALCALIGENES ATCC 31555, which contains in its molecule rhamnose, glucose, mannose and glucuronic acid, this biopolymer is described in British Patent No. 2,058,107; the biopolymer S139 produced by the strain PSEUDOMONAS ATCC 31644, which contains in its molecule rhamnose, glucose, mannose, galactose and galacturonic acid; this biopolymer is described in particular in U.S. Pat. No. 4,454,316; the biopolymer S198 produced by the strain ALCALIGENES ATCC 31853, which contains in its molecule rhamnose, glucose, mannose and glucuronic acid; this biopolymer is described in European Patent Application 64 354.

The biopolymer BM07 described in European Application EP 351 303, containing in its molecule units derived from glucose, galactose and pyruvic, succinic and acetic acids.

The biopolymer AM-2 which contains in its molecule glucose, rhamnose, mannose and glucuronic acid, described in European Application 127 698 or those described in European Application 79038 containing in their molecules glucose, galactose, mannose and glucuronic acid.

The scleroglucans used in accordance with the invention are neutral polysaccharides of microbial origin, obtained by aerobic fermentation of a glucose-containing medium, by a Sclerotium-type fungus and possessing the structure of a D-glucopyranose homopolymer.

The scleroglucans are these of the formula:

[chemical structure diagram]

where n (degree of polymerisation) ranges from 500 to 1600.

The scleroglucans used in accordance with the invention are represented by the products sold under the name ACTIGUM CS by SANOFI BIO INDUSTRIES and in particular ACTIGUM CS111, and under the name AMIGEL by ALBAN MULLER INTERNATIONAL. Other scleroglucans such as that treated with glyoxal and described in Patent Application FR 2,633,940 may also be used.

The surface-active agents used in the washing compositions conforming to the invention are chosen from anionic, amphoteric, zwitterionic or nonionic surface-active agents or mixtures thereof, having detergent properties.

Among the anionic surface-active agents, there may be mentioned the alkali metal salts, the ammonium salts, the amine salts, the aminoalcohol salts or the magnesium salts of the following compounds: alkyl ether sulphates, alkyl amidoether sulphates, alkyl aryl polyether sulphates, monoglyceride sulphates; alkyl sulphonates, alkyl amide sulphonates, alkyl aryl sulphonates, olefin sulphonates, paraffin sulphonates; alkyl sulphosuccinates, alkyl ether sulphosuccinates, alkyl amide sulphosuccinates; alkyl sulphosuccinamates; alkyl sulphoacetates; alkyl ether phosphates; acyl sarcosinates, and N-acyltaurates, the alkyl or acyl radical of these various compounds being composed of a carbon chain containing 12 to 20 carbon atoms.

Alkyl sulphates and alkyl phosphates whose alkyl radical contains 12 to 14 carbon atoms.

Among the anionic surface-active agents, fatty acid salts such as the salts of oleic, ricinoleic, palmitic or stearic acids; copra oil or hydrogenated copra oil acids; or acyl lactylates, whose acyl radical contains 8 to 20 carbon atoms, may also be mentioned.

Weakly anionic surface-active agents such as polyoxyalkylenated carboxylic ether acids, in particular those containing 2 to 50 ethylene oxide groups, may also be used.

The nonionic surface-active agents are chosen from polyethoxylated, polypropoxylated or polyglycerolated alcohols or α-diols or alkylphenols or fatty acids, with a fatty chain containing 8 to 18 carbon atoms, the number of ethylene oxide or propylene oxide groups being between 2 and 50 and the number of glycerol groups being between 2 and 30.

Copolymers of ethylene and propylene oxides; condensates of ethylene and propylene oxides with fatty alcohols; polyethoxylated fatty amides having preferably 2 to 30 mol of ethylene oxide; polyglycerolated fatty amides containing 1 to 5 glycerol groups and in particular 1.5 to 4; polyethoxylated fatty amines having preferably 2 to 30 mol of ethylene oxide; oxyethylenated sorbitan fatty acid esters having 2 to 30 mol of ethylene oxide; sucrose fatty acid esters, polyethylene glycol fatty acid esters, ($C_8$–$C_{18}$ alkyl) polyglycosides, amine oxides such as ($C_{10}$–$C_{14}$ alkyl)amine oxides or N-acylamidopropylmorpholine, may also be mentioned.

The preferred amphoteric or zwitterionic surface-active agents are the aliphatic secondary or tertiary amine derivatives in which the aliphatic radical is a linear or branched chain containing 8 to 18 carbon atoms and which contains at least one anionic water-solubilising carboxylate, sulphonate, sulphate, phosphate or phosphonate group; ($C_8$–$C_{20}$ alkyl) betaines, sulphobetaines, ($C_8$–$C_{20}$ alkyl)amido($C_1$–$C_6$ alkyl) betaines or ($C_8$–$C_{20}$ alkyl)amido($C_1$–$C_6$ alkyl) sulphobetaines.

Among the amine derivatives, there may be mentioned the products sold under the name NIRANOL, as described in Patents U.S. Pat. Nos. 2,528,378 and 2,781,354 and classified in the CTFA dictionary, 3rd edition, 1982, under the name amphocarboxyglycinates and amphocarboxypropionates.

The oils are used in the compositions conforming to the invention in proportions preferably of between 0.05 and 20%, and preferably between 0.1 and 1.0% by weight relative to the total weight of the composition.

The suspending agents defined in (b) used in accordance with the invention are present in proportions sufficient to ensure the suspension of the synthetic oils in the compositions, and preferably in proportions of between 0.1 and 20% by weight relative to the total weight of the composition, and in particular between 0.5 and 10%.

The surface-active agents are used in the compositions conforming to the invention in proportions sufficient to confer a detergent character on the composition and are preferably between 5 and 50% by weight relative to the total weight of the composition, and in particular between 8 and 35%.

The compositions according to the invention possess a pH generally between 2 and 9, and more particularly between 3 and 8.

The aqueous medium of the compositions is composed either of water or of a mixture of water and cosmetically acceptable solvents chosen from lower alcohols, alkylene glycols and glycol ethers.

The compositions according to the invention may also contain viscosity regulating agents, for example electrolytes such as sodium chloride or sodium xylenesulphonate, hydrotropic agents, thickeners such as cellulose derivatives, guar gum, hydroxypropylated guar gums.

These viscosity regulating agents are used in proportions ranging up to 10% by weight relative to the total weight of the composition, and preferably less than 5%.

The compositions conforming to the invention may optionally contain, in addition, other agents, provided that they do not alter the stability of the compositions, such as cationic surface-active agents, polymers or quaternised or nonquaternised proteins, silicone oils, waxes, resins or gum.

The polymers, cationic surface-active agents and quaternised or nonquaternised proteins, and the silicones, are used in the cosmetic or dermatological compositions according to the invention in proportions of between 0.05 and 6%, and preferably between 0.1 and 3% relative to the total weight of the composition.

The compositions according to the invention may also contain various adjuvants normally used in cosmetics, such as perfumes, preservatives, sequestering agents, foam stabilisers, propelling agents, colourants, acidifying or alkalinising agents or other adjuvants depending on the use envisaged.

The dermatological compositions in addition contain a substance which is active in the treatment of dermatological disorders.

The methods of washing and/or conditioning the hair or the skin consist in applying to them a composition as defined above, this application being followed by rinsing.

The compositions conforming to the invention may also be used as shower gels for washing the hair and the skin, in which case they are applied to wet skin and wet hair and are rinsed after application.

The following examples are intended to illustrate the invention without, however, being of a restrictive nature.

EXAMPLE 1

The following composition is prepared:

| | |
|---|---|
| Polyoxyethylenated ether carboxylic acid of formula RO($C_2H_4O$)$_n$$CH_2$COOH where R = $C_{12}$–$C_{14}$ alkyl and 1 = 4.5, sold by CHEM'Y under the name AKYPO RLM 45, containing 90% of active substance (AS) | 8.0 g AS |
| "Cocoamphocarboxyglycinate" (CTFA, 3rd edition, 1982) sold under the name MIRANOL C2M Conc. by MIRANOL in aqueous solution containing 38% of active substance (AS) | 4.0 g AS |

-continued

| | |
|---|---|
| Oxyethylenated propylene glycol oleate containing 55 mol of ethylene oxide esterified with oleic acid, sold under the name ANTIL 141 LIQUID by GOLDSCHMIDT | 2.0 g |
| Heptamethylnonane sold under the name ARLAMOL HD by ICI (of the formula (I) where n = 3) | 1.0 g |
| Preservatives, perfumes, colourants qs | |
| Water qs | 100.0 g |
| HCl qs pH 7.2 | |

This composition is used as shampoo for washing the hair.

EXAMPLE 2

The following composition is prepared:

| | |
|---|---|
| Alkylpolyglycoside sold by HORIZON CHEMICAL under the name APG 300 in a solution containing 50% of active substance (AS) | 12.5 g As |
| Ammonium lauryl sulphate | 5.0 g |
| ($C_{13}$–$C_{15}$ alkyl)oxydiethoxymethyl- monoethanolamide sold under the name AMINOL A15 by CHEM'Y | 3.0 g |
| Isohexadecane (of the formula (I) where n = 3) sold under the name PERMETHYL 101 A by PRESPERSE INC | 3.0 g |
| Preservatives, perfumes qs | |
| Water qs | 100.0 g |
| HCl qs pH 6.5 | |

This composition is used as shampoo for washing the hair.

EXAMPLE 3

The following composition is prepared:

| | |
|---|---|
| Polyoxyethylenated ether carboxylic acid of formula RO($C_2H_4O$)$_l$$CH_2$COOH where R = $C_{12}$–$C_{14}$ alkyl and l = 2.5 sold under the name AKYPO RLM 25 by CHEM'Y containing 90% of active substance (AS) | 5.0 g AS |
| Iso-octahexacontane (of the formula (I) where n = 16) sold under the name PERMETHYL 104 A by PRESPERSE INC | 0.15 g |
| Isohexadecane (of the formula (I) where n = 3) sold under the name PERMETHYL 101 A by PRESPERSE INC | 0.2 g |
| Ammonium lauryl sulphate | 6.0 g |
| Na lauryl sarcosinate sold under the name ORAMIX L30 by SEPPIC containing 30% of active substance (AS) | 5.0 g AS |
| PEG 6000 distearate | 2.0 g |
| Preservatives, perfumes qs | |
| Water qs | 100.0 g |
| HCl qs pH 5 | |

This composition is used as shampoo for washing the hair.

EXAMPLE 4

The following composition is prepared:

| | |
|---|---|
| Scleroglucan sold under the name ACTIGUM CS 11 by SANOFI BIO INDUSTRIES containing 90% of AS | 1.0 g As |
| Triethanolamine lauryl sulphate | 10.0 g |
| Lauryl betaine sold under the name DEHYTON AB 30 by HENKEL in an aqueous solution containing 32% of AS | 2.0 g As |
| Heptamethylnonane (of formula (I) where n = 3) sold under the name ARLAMOL HD by ICI | 1.0 g |
| Preservatives, perfumes qs | |
| Water qs | 100.0 g |
| NaOH qs pH 7.1 | |

This composition is used as shampoo for washing the hair.

EXAMPLE 5

The following composition is prepared:

| | |
|---|---|
| Triethanolamine lauryl sulphate | 15.0 g |
| Xanthan gum sold under the name KELTROL T by KELCO | 0.5 g |
| Sodium chloride | 2.0 g |
| N-Cetylpyridinium chloride, monohydrate | 1.0 g |
| Isoeicosane (of formula (I) where n = 4) sold under the name PERMETHYL 102 A by PRESPERSE INC | 2.5 g |
| Iso-octahexacontane sold under the name PERMETHYL 104 A by PRESPERSE INC | 0.7 g |
| Preservatives, perfumes qs | |
| Water qs | 100.0 g |
| NaOH qs pH 7 | |

This composition is used as shampoo for washing the hair.

EXAMPLE 6

The following composition is prepared:

| | |
|---|---|
| Oxyethylenated sodium lauryl ether sulphate containing 2.2 mol of ethylene oxide | 10.0 g |
| Ammonium lauryl sulphate | 8.0 g |
| Ethylene glycol $C_{16}$–$C_{18}$ diester (30 to 70 by weight) | 2.0 g |
| Copra acid monoisopropanolamide | 2.2 g |
| Sodium chloride | 2.5 g |
| Heptamethylnonane (of formula (I) where n = 3) sold under the name ARLAMOL HD by ICI | 1.0 g |
| Behenyltrimethylammonium chloride | 0.5 g |
| Preservatives, perfumes qs | |
| Water qs | 100.0 g |
| HCl qs pH 6 | |

This composition is used as shampoo for washing the hair.

EXAMPLE 7

The following composition is prepared:

| | |
|---|---|
| Polyoxyethylenated ether carboxylic acid of formula RO($C_2H_4O$)$_l$$CH_2$COOH where R = $C_{12}$–$C_{14}$ alkyl and l = 4.5 sold at 90% of active substance (AS) under the name RLM 45 by CHEM'Y | 10.0 g AS |
| "Cocoamphocarboxyglycinate" (CTFA, 3rd edition, 1982) sold under the name MIRANOL C2M Conc. by MIRANOL in an aqueous solution containing 38% of active substance (AS) | 6.0 g AS |
| Dimethylstearylamine oxide sold at 25% of active substance under the name AMMONYX SO by ONYX | 1.5 g AS |

-continued

| | |
|---|---|
| Isoeicosane (of formula (I) where n = 4) sold under the name PERMETHYL 102 A by PRESPERSE INC | 3.5 g |
| Preservatives, perfumes qs | |
| Water qs | 100.0 g |
| HCl qs pH 7 | |

This composition is used as shampoo for washing the hair.

EXAMPLE 8

The following composition is prepared:

| | |
|---|---|
| Oxyethylenated sodium lauryl ether sulphate containing 2.2 mol of ethylene oxide | 12.0 g |
| Sodium alpha-olefin sulphonate | 5.0 g |
| Copra monoisopropanolamide | 2.2 g |
| Sodium cetostearylsulphate ($C_{16}$–$C_{18}$ 50/50) | 1.5 g |
| Sodium chloride | 2.0 g |
| Heptamethylnonane (of formula (I) where n = 3) sold under the name ARLAMOL HD by ICI | 0.8 g |
| Preservatives, perfumes qs | |
| Water qs | 100.0 g |
| NaOH qs pH 6.5 | |

This composition is used as shampoo for washing the hair.

EXAMPLE 9

The following composition is prepared:

| | |
|---|---|
| ($C_{12}$–$C_{14}$ alkyl)polyglycoside (containing a mean glycoside number equal to 1.4) sold under the name TRITON CG 312 by SEPPIC | 35.0 g AS |
| Mixture of copra fatty acid monoethanolamide and glycerol sold under the name AMINOL CM by FINETEX | 5.0 g |
| Glycol distearate | 5.0 g |
| Isohexapentacontahectane (compound of formula (II) where m = 38) | 0.5 g |
| Isododecane (compound of formula (I) where n = 2) | 2.0 g |
| Preservatives, perfumes, colourants qs | |
| Water qs | 100.0 g |

The pH is adjusted to 6 with triethanolamine.

This composition is used as shower gel.

EXAMPLE 10

The following composition is prepared:

| | |
|---|---|
| Triethanolamine ($C_{12}$–$C_{14}$ alkyl)sulphate in an aqueous solution containing 40% of AS, sold under the name EMPICOL TL 40/FL by MARCHON | 12.0 g AS |
| Xanthan gum sold under the name KELTROL T by KELCO | 2.0 g |
| Glycol distearate | 2.5 g |
| Heptamethylnonane (compound of formula (I) where n = 3) | 5.0 g |
| Preservatives, perfumes, colourants qs | |
| Water qs | 100.0 g |

The pH is adjusted to 7 with triethanolamine.

This composition is used as shampoo.

EXAMPLE 11

The following composition is prepared:

| | |
|---|---|
| ($C_{12}$–$C_{14}$ alkyl)ether carboxylic acid containing 4.5 mol of ethylene oxide sold under the name AKYPO RLM 45 by LAMBERT RIVIERE | 10.0 g AS |
| Mixture of cocoylaminopropylbetaine and glycerol monolaurate in an aqueous solution containing 35% of AS, sold under the name TEGO BETAINE HS by GOLDSCHMIDT | 5.0 g AS |
| Sodium $C_{14}$–$C_{16}$ alpha-olefin sulphonate sold under the name WITCONATE AOS by WITCO | 5.0 g |
| Oxyethylenated propylene glycol oleate containing 55 mol of ethylene oxide and esterified by oleic acid, sold under the name ANTIL 141 LIQUID by GOLDSCHMIDT | 2.0 g |
| Isoeicosane (compound of formula (I) where n = 4)) | 0.05 g |
| Preservatives, perfumes, colourants qs | |
| Water qs | 100.0 g |

The pH is adjusted to 6 with triethanolamine.

This composition is used as shower gel.

EXAMPLE 12

The following composition is prepared:

| | |
|---|---|
| Sodium lauryl ether sulphate sold under the name EMPICOL ESB/3FL by MARCHON | 12.0 g AS |
| Cocoylbetaine in an aqueous solution containing 32% of AS | 5.0 g AS |
| Copra fatty acid monoisopropanolamine sold under the name EMPILAN CIS by MARCHON | 4.5 g |
| Glycol distearate | 3.0 g |
| Isohexadecane (compound of formula (I) where n = 3) | 10.0 g |
| Preservatives, perfumes, colourants qs | |
| Water qs | 100.0 g |

The pH is adjusted to 6 with hydrochloric acid.

This composition is used as shampoo.

We claim:

1. A method of washing and conditioning keratinous materials, comprising applying to said material at least one composition containing in an aqueous medium:

(A) at least one synthetic oil in proportions sufficient to confer softness and sheen to the keratinous materials, selected from the group consisting of:

(i) the isoparaffins of structure (I):

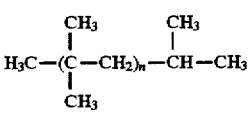

where n is between 2 and 16 inclusive; and (ii) a mixture of the isoparaffins of formula (I) with the isoparaffins of formula (II):

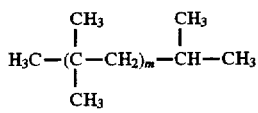

where m is not less than 18, the capillary viscosity of the oils defined in (i) and (ii) being less than 500 cP.s;

(B) an agent for suspending the synthetic oil defined in (A) in proportions sufficient to suspend the oil selected from the group consisting of:
i) the compounds of formula:

in which
a) R is a $C_{11}$–$C_{21}$ alkyl or alkenyl radical and X is a COOA group where A is a mono- or polyhydroxyalkyl radical derived from a $C_2$–$C_3$ polyol or a radical $CH_2CH_2SO_3M$;
a group CO $(OCH_2CH_2)_kOH$ where k has a value of between 2 and 150; or
a group

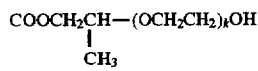

where k has a value of between 2 and 150;
b) R denotes a radical $R_3O(C_2H_4O)_lCH_2$ in which $R_3$ denotes a $C_{12}$–$C_{16}$ alkyl group and X a group $CONR_1R_2$ in which $R_1$ and $R_2$ represent hydrogen or $C_1$–$C_4$ hydroxyalkyl, at least one of $R_1$ and $R_2$ representing $C_1$–$C_4$ hydroxyalkyl and 1 has a value of 1 to 3 inclusive;
(ii) biopolysaccharides; and C) a surface-active agent possessing detergent properties present in proportions sufficient to confer detergent properties to the composition selected from the group consisting of:
(i) anionic surface active agents which are alkali metal salts, ammonium salts, amine salts, aminoalcohol salts or magnesium salts of alkyl ether sulphates, alkyl amidoether sulphates, alkyl aryl polyether sulphates, monoglyceride sulphates; alkyl sulphonates, alkyl amide sulphonates, alkyl aryl sulphonates, olefin sulphonates, paraffin sulphonates; alkyl sulphosuccinates, alkyl ether sulphosuccinates; alkyl amide sulphosuccinates; alkyl sulphosuccinamates, alkyl sulphoacetates; alkyl ether phosphates; acyl sarcosinates, and N-acyltaurates, the alkyl or acyl radical of these various compounds being composed of a carbon chain containing 12 to 20 carbon atoms; alkyl sulphates and alkyl phosphates whose alkyl radical contains 12 to 14 carbon atoms; fatty acid salts such as the salts of oleic, ricinoleic, palmitic or stearic acids; copra oil or hydrogenated copra oil acids; or acyl lactylates, whose acyl radical contains 8 to 20 carbon atoms;
(ii) non-ionic surface active agents which are polyethoxylated, polypropoxylated or polyglycerolated alcohol.; or a-diols or alkylphenols with a fatty chain containing 8 to 18 carbon atoms, the number of ethylene oxide or propylene oxide groups being between 2 and 50 and the number of glycerol groups being between 2 and 30; copolymers of ethylene and propylene oxides; condensates of ethylene and propylene oxides with fatty alcohols; polyglycerolated fatty amides containing 1 to 5 glycerol groups and in particular 1.5 to 4; polyethoxylated fatty amines having preferably 2 to 30 mol of ethylene oxide; oxyethylenated sorbitan fatty acid esters having 2 to 30 mol of ethylene oxide; sucrose fatty acid esters, ($C_8$–$C_{18}$alkyl)polyglycosides, ($C_{10}$–$C_{14}$alkyl)amine oxides or N-acylamidopropylmorpholine; and
(iii) amphoteric or zwitterionic surface active agents;
and in that after allowing the composition to act for a period of time, the treated materials are rinsed with water.

2. A method of treating keratinous material, comprising applying to the material a compound selected from the group consisting of:
a) the compounds of formula:

in which
(i) R is a $C_{11}$–$C_{21}$ alkyl or alkenyl radical and X is a COOA group when A is a mono- or polyhydroxyalklyl radical derived from a $C_2$–$C_3$ polyol or a radical $CH_2CH_2SO_3M$;
a group $CO(OCH_2CH_2)_kOH$ where k has a value of between 2 and 150; or
a group

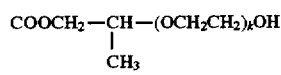

where k has a value of between 1 and 150;
(ii) R denotes a radical $R_3O(C_2H_4O)_lCH_2$ in which $R_3$ denotes a $C_{12}$–$C_{16}$ alkyl group and X a group $CONR_1R_2$, in which $R_1$ and $R_2$ represent hydrogen or $C_1$–$C_4$ hydroxyalkyl, at least one representing $C_1$–$C_4$ hydroxyalkyl and 1 has a value of 1 to 3 inclusive; and
(b) biopolysaccharides; in sufficient proportions to suspend synthetic oils selected from the group consisting of:
(i) the isoparaffins of formula:

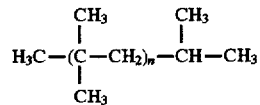

where n is between 2 and 16 inclusive; and
(ii) a mixture of the isoparaffins of formula (I) with the isoparaffins of formula (II):

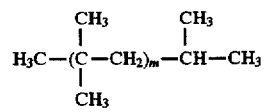

where m is not less than 18;

which are present in proportions sufficient to confer softness and sheen to the keratinous material, in an aqueous medium containing detergent surface-active-agents in proportions sufficient to confer washing properties, selected from the group consisting of:

(i) anionic surface active agents which are alkali metal salts, ammonium salts, amine salts, aminoalcohol salts or magnesium salts of alkyl ether sulphates, alkyl amidoether sulphates, alkyl aryl polyether sulphates, monoglyceride sulphates; alkyl sulphonates, alkyl amide sulphonates, alkyl aryl sulphonates, olefin sulphonates, paraffin sulphonates; alkyl sulphosuccinates, alkyl ether sulphosuccinates, alkyl amide sulphosuccinates; alkyl sulphosuccinamates; alkyl sulphoacetates; alkyl ether phosphates; acyl sarcosinates, and N-acyltaurates, the alkyl or acyl radical of these compounds being composed of a carbon chain containing 12 to 20 carbon atoms; alkyl sulphates and alkyl phosphates whose alkyl radical contains 12 to 14 carbon atoms; fatty acid salts such as the salts of oleic, ricinoleic, palmitic or stearic acids; copra oil or hydrogenated copra oil acids; or acyl lactylates;, whose acyl radical contains 8 to 20 carbon atoms;

(ii) non-ionic surface active agents which are polyethoxylated, polypropoxylated or polyglycerolated alcohols or α-diols or alkylphenols with a fatty chain containing 8 to 18 carbon atoms, the number of ethylene oxide or propylene oxide groups being between 2 and 50 and the number of glycerol groups being between 2 and 30; copolymers of ethylene and propylene oxides; condensates of ethylene and propylene oxides with fatty alcohols; polyglycerolated fatty amides containing 1 to 5 glycerol groups and in particular 1.5 to 4; polyethoxylated fatty amines having preferably 2 to 30 mol of ethylene oxide; oxyethylenated sorbitan fatty acid esters having 2 to 30 mol of ethylene oxide; sucrose fatty acid esters, ($C_8$–$C_{18}$ alkyl) polyglycosides, ($C_{10}$–$C_{14}$ alkyl) amine oxides or N-acylamidopropylmorpholime:

(iii) amphoteric or zwitterionic surface active agents.

* * * * *